US006432893B1

(12) United States Patent
Doi et al.

(10) Patent No.: US 6,432,893 B1
(45) **Date of Patent: *Aug. 13, 2002**

(54) METHOD FOR REMOVAL OF PROTEIN FROM CONTACT LENSES

(75) Inventors: Koji Doi; Takuya Nakajima, both of Kobe; Hisayuki Nakayama, Nishinomiya; Hiroshi Aki, Kobe, all of (JP)

(73) Assignee: Senju Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/529,716

(22) PCT Filed: Aug. 18, 1999

(86) PCT No.: PCT/JP99/04446

§ 371 (c)(1),
(2), (4) Date: Apr. 19, 2000

(87) PCT Pub. No.: WO00/11514

PCT Pub. Date: Mar. 2, 2000

(30) Foreign Application Priority Data

Aug. 21, 1998 (JP) .......................................... 10-251828

(51) Int. Cl.$^7$ ................................................ A61L 12/08

(52) U.S. Cl. ....................... 510/112; 510/112; 510/113; 510/114; 510/163; 510/164

(58) Field of Search ................................ 510/112, 113, 510/114, 163, 164

(56) References Cited

U.S. PATENT DOCUMENTS

| | | | | |
|---|---|---|---|---|
| 5,240,860 A | * | 8/1993 | Hoenes et al. | 436/111 |
| 5,840,250 A | * | 11/1998 | Park et al. | 422/28 |

FOREIGN PATENT DOCUMENTS

| | | | |
|---|---|---|---|
| JP | 62-150318 | | 7/1987 |
| JP | 62150318 | * | 7/1987 |
| JP | 7-168145 | | 7/1995 |
| JP | 8-5970 | | 1/1996 |
| JP | 8-327956 | | 12/1996 |

* cited by examiner

*Primary Examiner*—Yogendra N. Gupta
*Assistant Examiner*—Eisa Elhilo
(74) *Attorney, Agent, or Firm*—Wenderoth, Lind & Ponack, L.L.P.

(57) ABSTRACT

The present invention provides an agent for contact lenses, which contains an oxo-acid compound and/or a polyacid compound. The agent for contact lenses of the present invention can remove protein as, for example, a protein remover, irrespective of the kind of contact lens and without using a special cleaning device. In addition, washing with water after protein removal is not necessary.

29 Claims, No Drawings

METHOD FOR REMOVAL OF PROTEIN FROM CONTACT LENSES

TECHNICAL FIELD

The present invention relates to an agent for contact lenses. More particularly, the present invention relates to an agent for contact lenses, which contains an oxo-acid compound and/or a polyacid compound.

BACKGROUND ART

In recent years, various kinds of contact lenses, such as hard contact lens, oxygen permeable hard contact lens, soft contact lens and the like, have been widely used. These contact lenses easily become unclean due to the components contained in lacrimal fluid, such as protein, and require daily cleaning, sterilization and preservation.

The stain (e.g., protein) attached to the surface of a contact lens can be decomposed and removed by protease, and many cleaning agents have been proposed. For example, an agent in a solid form, which mainly contains a protease, such as tablet, granule, powder and the like, is supplied and an end user dissolves the agent each time in purified water and the like before use. This method requires dissolution of protease in a solid state every time the agent is used. As a result, the end user is forced to suffer from high cost and complicated handling.

In an attempt to solve such problems, some agents providing a protease in a solution state have been proposed as treating agents for contact lenses (JP-A-60-196722, JP-B-7-66113, JP-A-4-51015 and the like). In addition, a protein remover containing urea or a guanidine acid salt and specific reducing agent (JP-A-52-56852), a protein remover containing an aqueous alkali salt of hypobromous acid containing a specific amount of a compound such as citric acid and the like (JP-A-59-45339), a cleaning agent containing anionic surfactant such as alkylbenzenesulfonate and the like and a reducing agent such as sulfite and the like (JP-A-60-254114), a cleaning agent containing thiourea and surfactant and/or reducing agent (JP-A-61-51121) and the like have been proposed.

However, these protein removers and cleaning agents cause strong irritation to cornea, and require thorough rinsing with water after protein removal.

Further, a method has been proposed, which utilizes an electric field afforded to a lens to migrate stain deposit, thereby to clean and sterilize the contact lens (Japanese Patent Application under PCT laid-open under kohyo No. 9-511340).

This method requires previous application of an electric field to the contact lens, and also requires a special washing device.

Therefore, there is a demand on an agent for contact lenses which can remove protein irrespective of the kind of contact lens and without using a specific washing device, and which requires no water washing after protein removal.

DISCLOSURE OF THE INVENTION

The present inventors have conducted intensive studies in an attempt to achieve the above-mentioned objects and found that use of an oxo-acid compound and/or a polyacid compound as a protein remover enables removal of protein irrespective of the kind of contact lens and without using a specific washing device, and obviates water washing after protein removal, which resulted in the completion of the present invention.

Accordingly, the present invention provides the following.

(1) An agent for contact lenses comprising an oxo-acid compound and/or a polyacid compound as an active ingredient.

(2) The agent for contact lenses of (1), wherein the oxo-acid compound is an oxo-acid or a salt thereof or a hydrate thereof.

(3) The agent for contact lenses of (1), wherein the polyacid compound is a polyacid or a salt thereof or a hydrate thereof.

(4) The agent for contact lenses of (1) or (2), wherein the oxo-acid compound is an oxo-acid compound of a transition metal, typical metal or metalloid.

(5) The agent for contact lenses of (4), wherein the transition metal is vanadium, chromium, molybdenum or tungsten.

(6) The agent for contact lenses of (4), wherein the typical metal is tin.

(7) The agent for contact lenses of (4), wherein the metalloid is silicon or tellurium.

(8) The agent for contact lenses of (1) or (3), wherein the polyacid compound contains at least tungstic acid.

(9) The agent for contact lenses of any of (1) to (8), wherein the agent is a protein remover for contact lenses.

(10) The agent for contact lenses of any of (1) to (9), wherein the oxo-acid compound and/or the polyacid compound are/is contained in a proportion of 0.001–2.0 (W/V)%.

In the present specification, by the oxo-acid compound is meant an oxo-acid or a salt thereof or a hydrate thereof.

The center atom of the oxo-acid compound to be contained in the agent for contact lenses of the present invention is exemplified by transition metals, typical metals and metalloids.

Examples of the transition metal include the elements of groups 3 to 11 of the periodic table, preferably the elements of groups 5 and 6, such as vanadium (V), chromium (Cr), molybdenum (Mo), tungsten (W) and the like.

The typical metal is exemplified by the typical metals of groups 13 and 14 of the periodic table, preferably tin (Sn) and the like.

The metalloid is an element having the properties between a metal and a nonmetal. Examples thereof include silicon (Si), germanium (Ge), selenium (Se), antimony (Sb), tellurium (Te) and the like. Preferable metalloid includes silicon (Si), tellurium (Te) and the like.

Preferable oxo-acid includes vanadic acid ($HVO_3$), chromic acid ($H_2CrO_4$), molybdic acid ($H_2MoO_4$), tungstic acid ($H_2WO_4$), stannic acid ($H_2SnO_3$), silicic acid ($H_2SiO_3$), telluric acid ($H_2TeO_4$) and the like.

The oxo-acid that can be used for the agent for contact lenses of the present invention may be in the form of a salt with alkali metal (e.g., sodium, potassium and the like) or alkaline earth metal (e.g., magnesium, calcium and the like). The oxo-acid or a salt thereof may be a hydrate containing water of crystallization.

The polyacid compound to be contained in the agent for contact lenses of the present invention may be an isopolyacid compound or a heteropolyacid compound. The isopolyacid means a polyacid having a polynuclear structure wherein a single oxo-acid has been condensed. The heteropolyacid means a polyacid having a polynuclear structure wherein two or more kinds of oxo-acids have been condensed. The heteropolyacid has a structure comprising a condensed structure of an acid forming the skeleton (skeleton acid) and a small number of other kinds of atoms (hetero atom) contained in the center thereof and the like.

As used in this specification, "polyacid compound" refers to a polyacid or a salt thereof or a hydrate thereof.

The isopolyacid compound to be used in the present invention may be, for example, a condensed product of oxygen acid of an element, such as sulfur (S), silicon (Si), phosphorus (P), boron (B), a transition element belonging to the group 5 (vanadium (V), niobium (Nb), tantalum (Ta) and the like), a transition element belonging to the group 6 (chromium (Cr), molybdenum (Mo), tungsten (W) and the like) and the like. Preferably, it is a condensed product of oxygen acid of an element, such as vanadium (V), niobium (Nb), tantalum (Ta), molybdenum (Mo), tungsten (W) and the like. Specific examples thereof include heptaoxodisulfuric acid, pentaoxodisulfuric acid, disilicic acid, trisilicic acid, tetrasilicic acid, diphosphoric acid, triphosphoric acid, tetraphosphoric acid, polyphosphoric acid, tetraboric acid, pentaboric acid, hexavanadic acid, decavanadic acid, hexaniobic acid, dichromic acid, trichromic acid, tetrachromic acid, dimolybdic acid, hexamolybdic acid, heptamolybdic acid, octamolybdic acid, decamolybdic acid, dodecamolybdic acid, hexatungstic acid, decatungstic acid, paratungstic acid, metatungstic acid and the like. These isopolyacids may be a chain or a ring. When used in the form of a salt with alkali metal (e.g., sodium, potassium and the like) or alkaline earth metal (e.g., magnesium, calcium and the like), these isopolyacids become stable, and therefore, preferable. Examples of preferable salts of isopolyacid include sodium decavanadate, sodium decatungstate and the like. The isopolyacid or a salt thereof may be a hydrate containing water of crystallization.

The center atom of the skeleton acid of the heteropolyacid to be used for the present invention is an element such as vanadium (V), niobium (Nb), tantalum (Ta), molybdenum (Mo), tungsten (W) and the like, as in the case with isopolyacid, wherein hetero atom is not limited to a metal atom and includes an element such as phosphorus (P), silicon (Si), boron (B), germanium (Ge) and the like. The center atom of the skeleton acid may consist of one or more kinds of atoms.

The ratio of the number of the center atom of the hetero atom to that of the skeleton acid of the heteropolyacid is not particularly limited as long as they can form a polyacid having the above-mentioned polynuclear structure. It is preferably 1:6, 1:9, 1:12, 2:18 and the like.

Examples of heteropolyacid to be used in the present invention include those having one kind of the center atom of the skeleton acid, such as heteropolymolybdic acid, heteropolytungstic acid and the like, and those having two kinds of the center atoms of the skeleton acid, such as heteropolyvanadomolybdic acid, heteropolyvanadotungstic acid and the like.

Examples of heteropolymolybdic acid include $H_4(SiMo_{12}O_{40})$, $H_4(GeMo_{12}O_{40})$, $H_3(PMo_{12}O_{40})$, $H_8(SiMo_{11}O_{39})$, $H_8(GeMo_{11}O_{39})$, $H_7(PMo_{11}O_{39})$, $H_3(PMo_{12}O_{40})$, $H_6(P_2Mo_{18}O_{62})$, $H_6(P_2Mo_5O_{23})$ and the like.

Examples of heteropolytungstic acid include $H_5(BW_{12}O_{40})$, $H_4(SiW_{12}O_{40})$, $H_4(GeW_{12}O_{40})$, $H_3(PW_{12}O_{40})$, $H_9(BW_{11}O_{39})$, $H_8(SiW_{11}O_{39})$, $H_8(GeW_{11}O_{39})$, $H_7(PW_{11}O_{39})$, $H_6(P_2W_{18}O_{62})$, $H_{10}(P_2W_{17}O_{61})$, $H_6(P_2W_5O_{23})$, $H_{21}(P_4W_8O_{40})$ and the like.

Examples of heteropolyvanadomolybdic acid include $H_4(PMo_{11}VO_{40})$, $H_5(PMo_{10}V_2O_{40})$, $H_6(SiMo_{10}V_2O_{40})$, $H_6(PMo_9V_3O_{40})$ and the like. Examples of heteropolyvanadotungstic acid include $H_4(PW_{11}VO_{40})$, $H_5(SiW_{11}VO_{40})$, $H_5(PW_{10}V_2O_{40})$, $H_6(SiW_{10}V_2O_{40})$, $H_7(PW_9V_3O_{40})$, $H_5(PW_{10}V_2O_{40})$, $H_6(PW_6V_3O_{31})$, $H_7(SiW_9V_3O_{40})$ and the like.

The heteropolyacid that can be used in the present invention may be a salt with alkali metal (e.g., sodium, potassium and the like) or alkaline earth metal (e.g., magnesium, calcium and the like). It is preferably a salt in view of stability. Examples of preferable salt of heteropolyacid include $Na_8(GeW_{11}O_{39})$, $Na_5(PW_{10}V_2O_{40})$ and the like. The heteropolyacid or a salt thereof may be a hydrate containing water of crystallization.

The above-mentioned oxo-acid compound and/or polyacid compound can be used alone or in combination.

The agent for contact lenses of the present invention contains an oxo-acid compound and/or a polyacid compound in a proportion of 0.001–2.0 (W/V) %, preferably 0.01–1.0 (W/V) %. When the content is less than 0.001 (W/V) %, a sufficient protein removal effect cannot be achieved.

The agent for contact lenses of the present invention can be used for cleaning, protein removal, sterilization, preservation and the like of contact lenses. The agent can be used for respective uses for contact lenses, and further as a single agent for contact lenses for both cleaning and protein removal, and additionally for sterilization and/or preservation.

The agent for contact lenses of the present invention can contain other antimicrobial agent, buffer, isotonicity agent, surfactant, chelating agent, thickener, wetting agent and detergency improver as long as they do not act adversely to the object of the present invention.

Examples of antimicrobial agent include benzalkonium chloride, chlorhexidine gluconate, sorbic acid, a salt thereof, thimerosal, chlorobutanol, phenethyl alcohol, p-hydroxybenzoates and the like, which are selected according to the type of each contact lens, whether hard contact lens, oxygen permeable hard contact lens or soft contact lens, as long as they do not act adversely to the object of the present invention.

A buffer is used to make the pH of the agent for contact lenses of the present invention approximately 4–10, preferably 5–8. As a buffer, an acid and a salt thereof, or a base and a salt thereof, are combined by a conventional method to achieve a desired pH. Examples of the buffer include boric acid, sodium borate, citric acid, sodium citrate, tartaric acid, sodium tartrate, gluconic acid, sodium gluconate, acetic acid, sodium acetate, phosphoric acid, sodium monohydrogenphosphate, sodium dihydrogenphosphate, various amino acids and the like and combinations thereof.

The isotonicity agent is subject to no particular limitation as long as it is water soluble and shows no adverse effect such as irritation to the eye and the like. For example, sodium chloride, potassium chloride, calcium chloride, glycerol and the like can be used.

As the surfactant, any of nonionic surfactant, anionic surfactant, amphoteric surfactant and cationic surfactant can be used. The surfactant is used as a sterilizing power improver and detergency improver.

Examples of the anionic surfactant include sodium lauroylsarcosinate, triethanolamine lauroyl-L-glutamate, sodium myristylsarcosinate and the like; examples of amphoteric surfactant include lauryldimethylaminoacetic betaine, 2-alkyl-N-carboxymethyl-N-hydroxyethylimidazolium betaine, alkyldiaminoglycine hydrochloride and the like; examples of nonionic surfactant include polysorbate 80, polyoxyethylene hydrogenated castor oil 60, polyoxyl 40 stearate, polyoxyethylene lauryl ether and the like; and examples of cationic surfactant include benzethonium chloride, benzalkonium chloride, cetylpyridinium chloride and the like.

Examples of chelating agent include sodium edetate, sodium citrate, sodium condensed phosphate and the like.

Examples of thickener include hydroxyethylcellulose, methylcellulose, polyvinyl alcohol, polyvinylpyrrolidone and the like.

Examples of wetting agent include glycerol, polyethylene glycol, propylene glycol and the like.

According to the present invention, the form of the agent for contact lenses is subject to no particular limitation as long as it can take a liquid form when in use. It may be a liquid, semi-solid agent or a solid agent that can be stored for a long time and dissolved when in use. Examples of the solid agent include tablet, granule, powder and lyophilized product. In view of rapid dissolution and the aspects of sterilization and homogeniety of the composition, a lyophilized product is preferable. These agents can be produced according to a conventional method.

The content and pH of the aforementioned oxo-acid compound and/or polyacid compound and other components in a semi-solid agent or solid agent are those that make the content and pH of a liquid agent prepared when in use fall within the above range.

The agent for contact lenses of the present invention can be used for any contact lens. It may be any of hard contact lens, oxygen permeable hard contact lens and soft contact lens.

When the agent for contact lenses of the present invention is used as a cleaning agent of contact lenses, a contact lens after use is placed in this cleaning solution and kept immersed therein for 1 to 12 hours. After cleaning, the lens can be worn without washing with water.

EXAMPLES

The present invention is explained in more detail in the following by referring to some Examples. These Examples are for the purpose of explanation only, and do not limit the scope of the present invention in any way.

Example 1

Sodium vanadate ($NaVO_3$) sodium chromate ($Na_2CrO_4$ $4H_2O$), sodium molybdate ($Na_2MoO_4$ $2H_2O$), sodium tungstate ($Na_2WO_4$ $2H_2O$), sodium stannate ($Na_2SnO_3$ $3H_2O$), sodium silicate ($Na_2SiO_3$ $9H_2O$) and sodium tellurate ($Na_2TeO_4$ $2H_2O$) were respectively dissolved in distilled water. Hydrochloric acid was added to adjust the pH to 6 to 8, and distilled water was added in an appropriate amount to give 10 mM aqueous solutions.

Comparative Example 1

Distilled water was used for the comparative example.

Experimental Example 1

The following lysozyme chloride-staining solution was used.

| [lysozyme chloride-staining solution] | |
|---|---|
| lysozyme chloride | 0.1 g |
| sodium chloride | 0.9 g |
| sodium dihydrogenphosphate $12H_2O$ | 0.2 g |
| hydrochloric acid | appropriate amount |
| purified water | appropriate amount |
| total amount | 100 mL (pH 7.2) |

The above-mentioned lysozyme chloride-staining solution (10 mL) was charged in a test tube and the test tube was immersed in warm water (about 80° C.) for about 10 min to allow clouding of the solutioin. After cooling, the cloudy staining solution (about 50 $\mu$L) was dropped on the concave surface of hard contact lenses (main material: cellulose acetate butyrate) and the lenses were dried at 70° C. to give protein-stained lenses.

The lenses were rinsed with flowing water, and immersed in a 0.2% aqueous erythrosine solution for about 10 seconds to allow staining in pink. The stained lenses were rinsed with flowing water and dried. The difference in color from a clean transparent lens was measured with a colorimeter (CT-210, manufacture by Minolta) and taken as a color difference before washing, $\Delta E_1$.

The lenses were then immersed in respective aqueous solutions obtained in Example 1 and distilled water of Comparative Example 1 for 4 hours. The lenses were taken out, rinsed with flowing water, and again immersed in a 0.2% queous erythrosine solution for about 10 seconds to allow staining in pink. The colored lenses were rinsed with flowing water and dried. The difference in color from a clean transparent lens was measured with a colorimeter (CT-210, manufacture by Minolta) and taken as a color difference after washing, $\Delta E_2$. Three hard contact lenses were used for each solution of Example 1 and Comparative Example 1.

The cleaning rate was calculated by the following formula:

$$\text{cleaning rate }(\%) = \frac{\Delta E_1 - \Delta E_2}{\Delta E_1} \times 100$$

The test results of Example 1 and Comparative Example 1 are shown in Table 1.

TABLE 1

| | No. | ΔE1 | ΔE2 | cleaning rate (%) | average (%) |
|---|---|---|---|---|---|
| $NaVO_3$ | 1 | 13.02 | 7.24 | 44.4 | 40.3 |
| | 2 | 12.30 | 6.87 | 44.1 | |
| | 3 | 12.72 | 8.62 | 32.2 | |
| $Na_2CrO_4$ $4H_2O$ | 1 | 13.06 | 6.54 | 49.9 | 50.6 |
| | 2 | 13.15 | 6.17 | 53.1 | |
| | 3 | 13.20 | 6.75 | 48.9 | |
| $Na_2MoO_4$ $2H_2O$ | 1 | 12.62 | 8.37 | 33.7 | 23.7 |
| | 2 | 12.80 | 10.74 | 16.1 | |
| | 3 | 12.29 | 9.66 | 21.4 | |
| $Na_2WO_4$ $2H_2O$ | 1 | 14.04 | 8.70 | 38.0 | 43.4 |
| | 2 | 11.91 | 5.52 | 50.3 | |
| | 3 | 12.01 | 6.97 | 42.0 | |
| $Na_2SnO_3$ $3H_2O$ | 1 | 13.41 | 6.57 | 51.0 | 49.5 |
| | 2 | 13.56 | 7.02 | 48.2 | |
| | 3 | 12.25 | 6.22 | 49.2 | |

TABLE 1-continued

| | No. | ΔE1 | ΔE2 | cleaning rate (%) | average (%) |
|---|---|---|---|---|---|
| $Na_2SiO_3\ 9H_2O$ | 1 | 12.51 | 6.92 | 44.7 | 45.4 |
| | 2 | 13.30 | 7.14 | 46.3 | |
| | 3 | 13.74 | 7.52 | 45.3 | |
| $Na_2TeO_4\ 2H_2O$ | 1 | 15.82 | 7.39 | 53.3 | 55.5 |
| | 2 | 12.76 | 6.12 | 52.0 | |
| | 3 | 13.02 | 5.06 | 61.1 | |
| distilled | 1 | 11.95 | 12.18 | −1.9 | −1.4 |
| water | 2 | 15.11 | 15.82 | −4.7 | |
| | 3 | 12.07 | 11.76 | 2.6 | |

As is evident from Table 1, the salt of each oxo-acid in Example 1 was found to show a superior cleaning effect.

Example 2

Sodium dodecatungstosilicate ($Na_4(SiW_{12}O_{40})\ nH_2O$), 0.5 g, and sodium dihydrogenphosphate (anhydrous), 0.2 g, were dissolved in distilled water. Hydrochloric acid was added to adjust the pH to 7.0, and distilled water was added in an appropriate amount to make the amount 100 mL.

Example 3

The same procedure as in Example 2 was followed except that sodium dodecatungstophosphate ($Na_3(PO_412WO_3)\ nH_2O$) was used instead of sodium dodecatungstosilicate ($Na_4(SiW_{12}O_{40})\ nH_2O$).

Comparative Example 2

Distilled water was used for the comparative example.

Experimental Example 2

In the same manner as in Experimental Example 1, the test was performed to determine cleaning rate of Examples 2 and 3, and Comparative Example 2.

The test results of Examples 2 and 3, and Comparative Example 2 are shown in Table 2.

TABLE 2

| | No. | ΔE1 | ΔE2 | cleaning rate (%) | average (%) |
|---|---|---|---|---|---|
| $Na_4(SiW_{12}O_{40})$ | 1 | 17.20 | 7.80 | 54.7 | 54.0 |
| $nH_2O$ | 2 | 17.28 | 7.84 | 54.6 | |
| | 3 | 16.34 | 7.98 | 52.6 | |
| $Na_3(PO_412WO_3)$ | 1 | 17.19 | 8.31 | 51.7 | 53.7 |
| $nH_2O$ | 2 | 16.92 | 7.63 | 54.9 | |
| | 3 | 16.70 | 7.59 | 54.6 | |
| distilled | 1 | 17.65 | 13.03 | 26.2 | 9.5 |
| water | 2 | 17.41 | 17.86 | −2.6 | |
| | 3 | 15.69 | 14.90 | 5.0 | |

As is evident from Table 2, the salt of polyacids in Examples 2 and 3 were found to show a superior cleaning effect.

Example 4

A solution of the following recipe was used.

| | |
|---|---|
| disodium molybdate $2H_2O$ | 1.0 g |
| polyoxyethylene hydrogenated castor oil 60 | 0.2 g |
| boric acid | 1.2 g |
| sodium borate | 0.18 g |
| sodium edetate | 0.02 g |
| purified water | appropriate amount |
| total amount | 100 mL (pH 7.3) |

Comparative Example 3

Physiological saline was used for the comparative example.

Experimental Example 3

The following artificial lacrimal fluid was used.

| | |
|---|---|
| lysozyme chloride | 0.2 g |
| albumin (human) | 0.025 g |
| calcium chloride $2H_2O$ | 0.0036 g |
| sodium chloride | 0.9 g |
| sodium dihydrogenphosphate $12H_2O$ | 0.2 g |
| hydrochloric acid | appropriate amount |
| purified water | appropriate amount |
| total amount | 100 mL (pH 7.2) |

Soft contact lenses (hereinafter SCL) (main material: methyl methacrylate vinylpyrrolidone) were immersed in the aforementioned artificial lacrimal fluid at 37° C. for 20 hours to prepare protein-attached SCLS. The protein-attached SCLs were placed in a preservation case containing each solution of Example 4 and Comparative Example 3. After sterilization by boiling, the lenses were stood at room temperature. After 4 hours, SCLs were taken out and the amount of the attached protein was measured by Bicinchoninic acid protein assay. One SCL was used for each solution of Example 4 and Comparative Example 3.

The results are shown in Table 3.

TABLE 3

| | protein attached to SCL |
|---|---|
| Example 4 | 32.4% |
| Comparative Example 3 | 100.0% |

As is evident from Table 3, the solution of the recipe of Example 4 was confirmed to have significantly removed protein as compared to Comparative Example 3.

Example 5

The recipes in the following Table 4 are shown as examples. These solutions can be used for any of hard contact lens, oxygen permeable hard contact lens and soft contact lens.

TABLE 4

| Formulation Example | 1 | 2 | 3 | 4 | 5 | 6 | 7 | 8 | 9 | 10 |
|---|---|---|---|---|---|---|---|---|---|---|
| Disodium molybdate dihydrate (g) | 1.0 | 2.0 | | | 1.0 | | | | | 1.0 |
| sodium tungstate dihydrate (g) | | | 1.0 | 1.0 | | | | | | |
| Sodium tellurate (g) | | | | | | 1.0 | | | | |
| Sodium stannate (g) | | | | | | | 1.0 | | | |
| Sodium silicate (g) | | | | | | | | 1.0 | | |
| Sodium vanadate (g) | | | | | | | | | 1.0 | |
| POE(15) glyceryl monostearate (g) | 0.05 | 0.05 | 0.05 | 0.2 | | | | | | |
| POE(20) sorbitan monopalmitate (g) | | | | | 0.05 | 0.05 | 0.05 | | | |
| POE(60) sorbitol tetraoleate (g) | | | | | | | | 0.05 | | |
| POE hydrogenated castor oil (g) | | | | | | | | | 0.05 | |
| decaglyceryl monolaurate (g) | | | | | | | | | | 0.05 |
| Boric acid (g) | 1.2 | 1.2 | 1.2 | 1.2 | 1.2 | 1.2 | 1.2 | 1.2 | 1.2 | 1.2 |
| Sodium borate | q.s. | q.s. | q.s. | q.s. | q.s. | q.s. | q.s. | q.s. | q.s. | q.s. |
| Sodium edetate (g) | 0.02 | 0.02 | 0.02 | 0.02 | 0.02 | 0.02 | 0.02 | 0.02 | 0.02 | 0.02 |
| Purified water | q.s. | q.s. | q.s. | q.s. | q.s. | q.s. | q.s. | q.s. | q.s. | q.s. |
| pH | 7.3 | 7.3 | 7.3 | 7.3 | 7.3 | 7.3 | 7.3 | 7.3 | 7.3 | 7.3 |
| Total amount | | | | | | 100 ml | | | | |

Industrial Applicability

Inasmuch as the agent for contact lenses of the present invention contains a specific oxo-acid compound and/or a polyacid compound as an active ingredient for, for example, a protein remover, protein can be removed irrespective of the kind of contact lens and without a special cleaning device. In addition, washing with water after protein removal is not necessary.

This application is based on application No. 251828/1998 filed in Japan, the contents of which are incorporated hereinto by reference.

What is claimed is:

1. A method of removing protein on a contact lens, which comprises contudng a contact lens with an agent for contact lens comprising a metallic oxo-acid compound or a metallic polyacid compound or a combination thereof as a protein remover.

2. The method of claim 1, wherein the metallic oxo-acid compound is a metallic oxo-acid or a salt thereof or a hydrate thereof.

3. The method of claim 1, wherein the metallic polyacid compound is a metallic polyacid or a salt thereof or a hydrate thereof.

4. The method of claim 1, wherein the metallic oxo-acid compound contains a transition metal, a Group 13 or 14 metal, or a metalloid.

5. The method of claim 4, wherein the transition metal is vanadium, molybdenum or tungsten.

6. The method of claim 4, wherein the Group 13 or 14 metal is tin.

7. The method of claim 4, wherein the metalloid is silicon or tellurium.

8. The method of claim 1, wherein the metallic polyacid compound contains at least vanadium, molybdenum or tungsten.

9. The method of any one of claims 1 to 8, wherein the metallic oxo-acid compound or the metallic polyacid compound or a combination thereof are each contained in a proportion of 0.001–2.0 (W/V) %.

10. The method of any one of claims 1 to 8, which comprises immersing and boiling a contact lens in the agent for contact lens.

11. The method of claim 1, wherein the agent for contact lens is free of hydrogen peroxide, sodium perborate, sodium hypochlorite and sodium chlorite.

12. A method of cleaning a contact lens, which comprises immersing and standing a contact lens in an agent for contact lens comprising a metallic oxo-acid compound or a metallic polyacid compound or a combination thereof as a protein remover.

13. The method of claim 12, wherein the metallic oxo-acid compound is a metallic oxo-acid or a salt thereof or a hydrate thereof.

14. The method of claim 12, wherein the metallic polyacid compound is a metallic polyacid or a salt thereof or a hydrate thereof.

15. The method of claim 12, wherein the metallic oxo-acid compound contains of a transition metal, a Group 13 or 14 metal, or a metalloid.

16. The method of claim 15, wherein the transition metal is vanadium, molybdenum or tungsten.

17. The method of claim 15, wherein the Group 13 or 14 metal is tin.

18. The method of claim 15, wherein the metalloid is silicon or tellurium.

19. The method of claim 12, wherein the metallic polyacid compound contains at least vanadium, molybdenum or tungsten.

20. The method of any one of claims 12 to 19, wherein the metallic oxo-acid compound or the metallic polyacid compound or a combination thereof are each contained in a proportion of 0.001–2.0 (WV) %.

21. A method of cleaning and sterilizing a contact lens, which comprises immersing and boiling a contact lens in an agent for contact lens comprising a metallic oxo-acid compound or a metallic polyacid compound or a combination thereof as a protein remover.

22. The method of claim 21, wherein the metallic oxo-acid compound is a metallic oxo-acid or a salt thereof or a hydrate thereof.

23. The method of claim 21, wherein the metallic polyacid compound is a metallic polyacid or a salt thereof or a hydrate thereof.

24. The method of claim 21, wherein the metallic oxo-acid compound contains a transition metal, a Group 13 or 14 metal, or a metalloid.

25. The method of claim 24, wherein the transition metal is vanadium, molybdenum or tungsten.

26. The method of claim 24, wherein the Group 13 or 14 metal is tin.

27. The method of claim 24, wherein the metalloid is silicon or tellurium.

28. The method of claim 21, wherein the metallic polyacid compound contains at least vanadium, molybdenum or tungsten.

29. The method of any one of claims 21 to 28, wherein the metallic oxo-acid compound or the metallic polyacid compound or a combination thereof are each contained in a proportion of 0.001–2.0 (WV) %.

* * * * *